United States Patent
Karube et al.

(10) Patent No.: US 10,611,710 B2
(45) Date of Patent: Apr. 7, 2020

(54) METHOD FOR PRODUCING 1-CHLORO-1,2-DIFLUOROETHYLENE

(71) Applicant: DAIKIN INDUSTRIES, LTD., Osaka (JP)

(72) Inventors: Daisuke Karube, Osaka (JP); Satoshi Ohishi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/314,915

(22) PCT Filed: Jul. 11, 2017

(86) PCT No.: PCT/JP2017/025319
§ 371 (c)(1),
(2) Date: Jan. 3, 2019

(87) PCT Pub. No.: WO2018/012511
PCT Pub. Date: Jan. 18, 2018

(65) Prior Publication Data
US 2019/0169101 A1    Jun. 6, 2019

(30) Foreign Application Priority Data
Jul. 11, 2016    (JP) .................... 2016-136600

(51) Int. Cl.
*C07C 17/25*    (2006.01)
*C07C 21/18*    (2006.01)
*C07B 61/00*    (2006.01)

(52) U.S. Cl.
CPC ............. *C07C 17/25* (2013.01); *C07C 21/18* (2013.01); *C07B 61/00* (2013.01)

(58) Field of Classification Search
CPC ................................. C07C 17/25; C07C 21/18
See application file for complete search history.

(56) References Cited

U.S. PATENT DOCUMENTS 2,716,109 A    8/1955  Ruh et al.
5,180,860 A  * 1/1993  Fernandez .............. C07C 17/25
                                                        570/155

FOREIGN PATENT DOCUMENTS

JP    2014-141538    8/2014
JP    2015-120670    7/2015

OTHER PUBLICATIONS

Petrov, Viacheslav A, Selective Reduction of Halopolyfluorocarbons by Organosilicon Hydrides, Journal of Organic Chemistry (1998), 63(21), 7294-7297.*
International Search Report dated Sep. 19, 2017 in International (PCT) Application No. PCT/JP2017/025319 with English translation.
Henne et al., "Fluorochloroethanes and Fluorochloroethylenes. II", Journal of the American Chemical Society, vol. 58, pp. 402-403, 1936.
Birchall et al., "Polyfluoroarenes. Part III. A New Synthesis of Hexafluorobenzene", Journal of the Chemical Society, pp. 2204-2206, 1961.
Sargeant, "Fluorocyclopropanes. I. Preparation and Nuclear Magnetic Resonance Spectra", The Journal of Organic Chemistry, vol. 35. No. 3, pp. 678-682, 1970.
Boguslayskaya et al., "Reactions of Chlorine Monofluoride. II. Regiospecificity and Stereochemistry of the Substitution of Bromine Atoms by Fluorine in Halogen-Substituted Alkanes and Esters", Zhurnal Organicheskoi Khimii, vol. 18, No. 5, pp. 938-945, 1982.
Extended European Search Report dated Dec. 10, 2019 in corresponding European Patent Application No. 17827638.2.
Morikawa et al., "Preparation of 1,1,1,2- or 1,1,2,2-Tetrafluoroethane by hydrogenation of chlorofluoroethanes", Chemical Abstracts, Chemical Abstracts Service (CAS), US, vol. 112, No. 9, p. 724, 1990.
Ishikawa et al., "Pulse-Duration Effects on Competitive Reactions in Infrared Multiple-Photon Decomposition of $CH_2ClCHClF$ and $CHClFCHClF$", The Journal of Physical Chemistry, vol. 90, No. 21, pp. 5067-5071, 1986.

* cited by examiner

*Primary Examiner* — Jafar F Parsa
(74) *Attorney, Agent, or Firm* — Wenderoth, Lind & Ponack, L.L.P.

(57) ABSTRACT

The present invention provides a method for efficiently producing 1-chloro-1,2-difluoroethylene at low cost. Specifically, the present invention provides a method for producing 1-chloro-1,2-difluoroethylene, including the step of dehydrohalogenating chlorofluoroethane represented by formula (1) $CFClX^1$—$CHFX^2$ wherein $X^1$ and $X^2$ are different from each other and represent H, F, or Cl; and either $X^1$ or $X^2$ is H.

7 Claims, No Drawings

METHOD FOR PRODUCING 1-CHLORO-1,2-DIFLUOROETHYLENE

TECHNICAL FIELD

The present invention relates to methods for producing 1-chloro-1,2-difluoroethylene.

BACKGROUND ART

1-Chloro-1,2-difluoroethylene (CFCl=CHF; HCFO-1122a) shows promise as a refrigerant with low global-warming potential (GWP) (see PTL 1).

Examples of known methods for producing 1-chloro-1,2-difluoroethylene include a method in which dehalogenation is performed on a halogenated ethane represented by the formula CFClX—CHFX wherein each X represents Cl, Br, or I (a starting material) in the presence of a catalyst, such as zinc; and a method in which 1,2-dichloro-difluoroethylene (CFCl=CFCl) is reduced using a silane compound (see PTL 2 and NPL 1 to 3). However, such methods, due to the use of zinc as a catalyst, must employ batch reaction, which generates a considerable amount of insoluble waste that requires cumbersome treatment, thus resulting in high costs. Additionally, the halogenated ethane used as a starting material, for example, 1,1,2-trichloro-1,2-difluoroethane (CFCl$_2$—CHFCl), is produced by performing F$_2$ addition reaction on trichloroethylene (CCl$_2$=CHCl), and this reaction uses substances that require special care in handling, such as F$_2$ and CoF$_3$.

Another known method for producing 1-chloro-1,2-difluoroethylene dehydrochlorinates 1,2-dichloro-1,2-difluoroethane (CHFCl—CHFCl; HCFC-132) in a liquid phase (see PTL 3 and NPL 4). However, this method uses a considerable amount of a reagent for performing dehydrochlorination, and also generates a considerable amount of chlorides that cannot be recycled for reaction.

Due to these problems in the art, there is demand for a method for efficiently producing 1-chloro-1,2-difluoroethylene at low cost.

CITATION LIST

Patent Literature

PTL 1: JP2014-141538A
PTL 2: U.S. Pat. No. 2,716,109
PTL 3: JP2015-120670A

Non-Patent Literature

NPL 1: Journal of the American Chemical Society, 1936, vol. 58, p. 403
NPL 2: Journal of the Chemical Society, 1961, p. 2204
NPL 3: Journal of Organic Chemistry, 1970, vol. 35, p. 678
NPL 4: Zhurnal Organicheskoi Khimii, 18(5), 938-945, 1982

SUMMARY OF INVENTION

Technical Problem

The present invention was made in view of the problems in the art described above, and an object of the invention is to provide a method for efficiently producing 1-chloro-1,2-difluoroethylene at low cost.

Solution to Problem

The present inventors conducted extensive research to achieve the object, and found that 1-chloro-1,2-difluoroethylene can be efficiently produced at low cost by dehydrohalogenating a chlorofluoroethane represented by formula (1) CFClX$^1$—CHFX$^2$ wherein X$^1$ and X$^2$ are different from each other and represent H, F, or Cl; and either X$^1$ or X$^2$ is H. The present inventors conducted further research on the basis of this finding and completed the invention.

Specifically, the present invention includes representative inventions described in the following items.

Item 1

A method for producing 1-chloro-1,2-difluoroethylene, the method comprising the step of dehydrohalogenating a chlorofluoroethane represented by formula (1) CFClX$^1$—CHFX$^2$ wherein X$^1$ and X$^2$ are different from each other and represent H, F, or Cl; and either X$^1$ or X$^2$ is H.

Item 2

The method according to Item 1, wherein the dehydrohalogenation step is performed in a gas phase.

Item 3

The method according to Item 1 or 2, wherein the chlorofluoroethane is at least one member selected from the group consisting of 1-chloro-1,2,2-trifluoroethane, 1-chloro-1,1,2-trifluoroethane, 1,2-dichloro-1,2-difluoroethane, and 1,1-dichloro-1,2-difluoroethane.

Item 4

The method according to any one of Items 1 to 3, wherein the dehydrohalogenation step is performed in the presence of a catalyst.

Item 5

The method according to any one of Items 1 to 3, wherein the dehydrohalogenation step is performed in the absence of a catalyst.

Item 6

The method according to any one of Items 1 to 5, wherein the dehydrohalogenation step is performed at a temperature of 200 to 550° C.

Item 7

The method according to any one of Items 1 to 6, wherein the chlorofluoroethane is 1-chloro-1,2,2-trifluoroethane and/or 1-chloro-1,1,2-trifluoroethane, and the dehydrohalogenation step is a dehydrofluorination step.

Item 8

A method for producing 1-chloro-1,2-difluoroethylene, the method comprising the steps of reducing a chlorotrifluoroethylene and/or 1,1,2-trichloro-1,2,2-trifluoroethane to generate a chlorotrifluoroethane represented by formula (2) CFClX$^3$—CHFX$^4$ wherein X$^3$ and X$^4$ are different from each other and represent H or F, and dehydrofluorinating the chlorotrifluoroethane obtained in the previous step.

Advantageous Effects of Invention

The present invention can efficiently produce 1-chloro-1,2-difluoroethylene at low cost.

DESCRIPTION OF EMBODIMENTS

The following describes the present invention in detail.

First Invention

The present invention encompasses a method for producing 1-chloro-1,2-difluoroethylene (CFCl=CHF; HCFO- 1122a). In this specification, the method may be referred to as "the first method of the present invention."

The product of the first method of the present invention, 1-chloro-1,2-difluoroethylene, has geometric isomers such as cis (Z) form and trans (E) form. In this specification, the cis form of 1-chloro-1,2-difluoroethylene may be referred to as "cis-1-chloro-1,2-difluoroethylene," and the trans form of 1-chloro-1,2-difluoroethylene may be referred to as "trans-1-chloro-1,2-difluoroethylene." A mixture of the cis form and the trans form of 1-chloro-1,2-difluoroethylene, or 1-chloro-1,2-difluoroethylene that is not distinguished as to whether it is the cis form or the trans form may be simply referred to as "1-chloro-1,2-difluoroethylene."

The first method of the present invention comprises the step of dehydrohalogenating a chlorofluoroethane represented by formula (1) $CFClX^1$—$CHFX^2$ wherein $X^1$ and $X^2$ are different from each other and represent H, F, or Cl; and either $X^1$ or $X^2$ is H. In this specification, the chlorofluoroethane represented by formula (1) may be simply referred to as "chlorofluoroethane." In this specification, the step described above may be referred to as the "dehydrohalogenation step."

Due to the dehydrohalogenation step, a hydrogen halide is detached from the chlorofluoroethane represented by formula (1), thereby obtaining 1-chloro-1,2-difluoroethylene. In this specification, "hydrogen halide" means hydrogen fluoride (HF) or hydrogen chloride (HCl).

The dehydrohalogenation step is preferably performed in a gas phase. Performing the dehydrohalogenation step in a gas phase generates trans-1-chloro-1,2-difluoroethylene at a higher selectivity, compared with cis-1-chloro-1,2-difluoroethylene.

$X^1$ and $X^2$ in formula (1) are different from each other and represent H, F, or Cl; and either $X^1$ or $X^2$ is H. For example, when $X^1$ is H, $X^2$ is F or Cl. When $X^1$ is F or Cl, $X^2$ is H.

Examples of the chlorofluoroethane represented by formula (1) include 1-chloro-1,2,2-trifluoroethane (HCFC-133) represented by the formula $CHFCl$—$CHF_2$, 1-chloro-1,1,2-trifluoroethane (HCFC-133b) represented by the formula $CF_2Cl$—$CH_2F$, 1,2-dichloro-1,2-difluoroethane (HCFC-132) represented by the formula $CHFCl$—$CHFCl$, and 1,1-dichloro-1,2-difluoroethane (HCFC-132c) represented by the formula $CFCl_2$—$CH_2F$.

The chlorofluoroethane represented by formula (1) for use as a starting material in the dehydrohalogenation step may be one compound or a combination of two or more compounds of those listed above as examples of the chlorofluoroethane. The mixture ratio of two or more compounds of such a combination is not particularly limited, and can be suitably determined.

The dehydrohalogenation step is broadly classified into a dehydrofluorination reaction in which hydrogen fluoride is detached from the chlorofluoroethane represented by formula (1), and a dehydrochlorination reaction in which hydrogen chloride is detached from the chlorofluoroethane represented by formula (1), depending on the starting material for use (specifically, the type of the chlorofluoroethane represented by formula (1)). In this specification, the term "dehydrohalogenation" includes the dehydrofluorination reaction in which hydrogen fluoride is detached and the dehydrochlorination reaction in which hydrogen chloride is detached. Dehydrohalogenation refers to one of these two reactions, or both, depending on the starting material for use. For example, when 1-chloro-1,2,2-trifluoroethane, 1-chloro-1,1,2-trifluoroethane, or the like is used as a starting material, the dehydrohalogenation refers to the dehydrofluorination reaction; when 1,2-dichloro-1,2-difluoroethane, 1,1-dichloro-1,2-difluoroethane, or the like is used, the dehydrohalogenation refers to the dehydrochlorination reaction; when at least one member of 1-chloro-1,2,2-trifluoroethane and 1-chloro-1,1,2-trifluoroethane and at least one member of 1,2-dichloro-1,2-difluoroethane and 1,1-dichloro-1,2-difluoroethane are mixed for use, the dehydrohalogenation refers to both the dehydrofluorination reaction and the dehydrochlorination reaction.

The dehydrohalogenation step may be performed in the presence of a catalyst or in the absence of a catalyst. The dehydrohalogenation step is preferably performed in the presence of a catalyst because doing so can improve the selectivity for and the yield of 1-chloro-1,2-difluoroethylene.

When the dehydrohalogenation step is performed in the presence of a catalyst, the catalyst for use is not particularly limited, and may be a known catalyst that exhibits catalytic activity in the dehydrohalogenation reaction. For such a catalyst, dehydrohalogenation catalysts can be used. Examples of dehydrohalogenation catalysts include dehydrofluorination catalysts that exhibit catalytic activity in the dehydrofluorination reaction and dehydrochlorination catalysts that exhibit catalytic activity in the dehydrochlorination reaction.

Examples of dehydrofluorination catalysts include halides, oxides, and fluorinated oxides of metals, such as transition metals, aluminum, elemental metals that belong to group 14, and elemental metals that belong to group 15. These dehydrofluorination catalysts are considered to have an effect of accelerating dehydrofluorination reaction due to the high affinity of the metal elements for the detached fluorine atom.

Examples of transition metals include titanium, vanadium, chromium, manganese, iron, cobalt, nickel, niobium, molybdenum, tantalum, and zirconia. Examples of elemental metals that belong to group 14 include tin and lead. Examples of elemental metals that belong to group 15 include antimony and bismuth. Examples of halides include fluorides and chlorides.

Specific examples of halides of the metals described above include titanium(IV) chloride, chromium(III) fluoride, chromium(III) chloride, iron(III) chloride, niobium(V) chloride, molybdenum(V) chloride, tantalum(V) chloride, aluminum fluoride, tin(IV) chloride, antimony(V) fluoride, antimony(V) chloride, and antimony(III) chloride. Specific examples of oxides of the metals described above include chromium(III) oxide and aluminum oxide. Specific examples of fluorinated oxides of the metals described above include fluorinated chromium(III) oxide and fluorinated aluminum oxide.

Of the dehydrofluorination catalysts listed above, in particular, chromium(III) oxide, aluminum oxide, fluorinated chromium(III) oxide, and fluorinated aluminum oxide are preferable. Chromium(III) oxide and fluorinated chromium(III) oxide for use may be in the form of crystalline chromium oxide, amorphous chromium oxide, and the like.

The dehydrofluorination catalysts may be used singly or in any combination of two or more.

Examples of dehydrochlorination catalysts include halides, oxides, and fluorinated oxides of metals, such as alkali metals, alkaline earth metals, and divalent or monovalent transition metals; and activated carbon.

Examples of alkali metals include lithium, sodium, potassium, and cesium. Examples of alkaline earth metals include magnesium, calcium, strontium, and barium. Examples of divalent or monovalent transition metals include cobalt, nickel(II), copper(II), zinc(II), and silver. Examples of halides include fluorides and chlorides.

Specific examples of halides of the metals described above include magnesium fluoride, magnesium chloride, nickel(II) fluoride, nickel(II) chloride, zinc(II) fluoride, zinc (II) chloride, copper(II) fluoride, and copper(II) chloride. Specific examples of oxides of the metals described above include magnesium oxide, nickel(II) oxide, zinc(II) oxide, and copper(II) oxide. Examples of fluorinated oxides of the metals include fluorinated zinc(II) oxide, fluorinated magnesium oxide, and fluorinated nickel(II) oxide.

Of the dehydrochlorination catalysts listed above, in particular, magnesium fluoride, zinc(II) oxide, nickel(II) oxide, and activated carbon are preferable.

The dehydrochlorination catalysts may be used singly or in any combination of two or more.

The dehydrofluorination catalysts and dehydrochlorination catalysts may be used in combination. In particular, when a chlorofluoroethane (e.g., 1-chloro-1,2,2-trifluoroethane and 1-chloro-1,1,2-trifluoroethane) that generates 1-chloro-1,2-difluoroethylene through the dehydrofluorination reaction and a chlorofluoroethane (e.g., 1,1-dichloro-1,2-difluoroethane) that generates 1-chloro-1,2-difluoroethylene through the dehydrochlorination reaction are used in combination as a starting material, it is preferable to use a combination of a dehydrofluorination catalyst and a dehydrochlorination catalyst.

The dehydrohalogenation catalysts for use may be supported on a carrier. Such a carrier is not particularly limited, and may be a known carrier for use in dehydrohalogenation catalysts. Examples of carriers include porous aluminosilicate, such as zeolite, aluminum oxide, silicon oxide, activated carbon, titanium oxide, zirconia oxide, zinc oxide, and aluminum fluoride. The carriers may be used singly or in the form of composite composed of two or more carriers. Examples of the combination of a dehydrohalogenation catalyst and a carrier (a dehydrohalogenation catalyst on a carrier) include chromium(III) oxide on aluminum oxide, chromium(III) oxide on aluminum fluoride, and chromium (III) oxide on activated carbon. Examples of the combination of two dehydrohalogenation catalysts and a carrier (a dehydrohalogenation catalyst and a dehydrohalogenation catalyst on a carrier) include cobalt(II) chloride and chromium(III) oxide on aluminum oxide, and nickel(II) chloride and chromium(III) oxide on aluminum oxide.

The dehydrohalogenation step is preferably performed in a reactor. The reactor is not particularly limited. For example, a continuous reactor, such as an adiabatic reactor, and a multitubular reactor heated with a heating medium, may be used. The reactor for use is also preferably made of a material resistant to the corrosive action of hydrogen fluoride or hydrogen chloride generated in the dehydrohalogenation step.

When a catalyst is used in the dehydrohalogenation step, the method for allowing the catalyst to be present in the reactor is not particularly limited, as long as the starting material sufficiently comes into contact with the catalyst. Examples of the method include a method by which a reactor is packed with a catalyst.

When a catalyst is used in the dehydrohalogenation step, the chlorofluoroethane represented by formula (1) and a catalyst are brought into contact with each other. The method for bringing the chlorofluoroethane represented by formula (1) and a catalyst into contact with each other is not particularly limited. For example, the chlorofluoroethane represented by formula (1) and a catalyst can be brought into contact by supplying the chlorofluoroethane represented by formula (1) to a reactor in a gas phase.

The chlorofluoroethane represented by formula (1) may be supplied as is to a reactor, or may be supplied to a reactor together with a gas inert to the starting material, the catalyst etc. when the chlorofluoroethane must be diluted for some reason, such as to control the reactivity. Examples of the inert gas include nitrogen, helium, and argon.

When the chlorofluoroethane represented by formula (1) is supplied to a reactor together with an inert gas, the concentration of the inert gas is not particularly limited. For example, the concentration of the inert gas may be 10 to 99 mol % of the total amount of the gas component supplied to the reactor.

When a catalyst is used in the dehydrohalogenation step, oxygen may be supplied to the reactor to maintain the catalytic activity for an extended period of time. The oxygen supplied to the reactor may be an oxygen gas alone or air containing oxygen. The amount of oxygen supplied may be, for example, about 0.1 to 50 mol %, and preferably 1 to 20 mol % of the total amount of the gas component supplied to the reactor.

Additionally, when a catalyst is used in the dehydrohalogenation step, anhydrous hydrogen fluoride may be supplied to the reactor, for example, for the purpose of increasing the catalytic activity of the dehydrohalogenation catalyst. The amount of anhydrous hydrogen fluoride supplied may be about 1 to 100 mols per mol of the chlorofluoroethane represented by formula (1) supplied to the reactor.

The reaction temperature in the dehydrohalogenation step is not particularly limited, as long as the reaction to generate 1-chloro-1,2-difluoroethylene from the chlorofluoroethane represented by formula (1) occurs. The specific reaction temperature is, for example, about 200 to 550° C., preferably about 250 to 450° C., and more preferably about 300 to 450° C. The reaction temperature within these ranges can maintain excellent conversion of the starting material, and is likely to reduce the generation of impurities and deterioration of catalytic activity caused by the altered catalyst. A higher reaction temperature is likely to generate trans-1-chloro-1,2-difluoroethylene. Thus, if a high selectivity for the trans form of 1-chloro-1,2-difluoroethylene is desired, the reaction temperature is preferably 300° C. or more.

The reaction time in the dehydrohalogenation step is not particularly limited. When the dehydrohalogenation step is performed in the absence of a catalyst, the retention time is preferably about 1 to 500 sec, and more preferably 30 to 300 sec: the retention time is represented by the ratio of volume V (cc) of a heated reactor to the total flow rate $F_0$ of a gas supplied to the reactor (a flow rate at 0° C. and 0.1 MPa; cc/sec) (V/$F_0$). When the dehydrohalogenation step is performed in the presence of a catalyst, the contact time is preferably about 1 to 500 g·sec/cc, and more preferably about 30 to 300 g·sec/cc: the contact time is represented by the ratio of the amount of a packed catalyst W (g) to the total flow rate $F_0$ of a gas supplied to a reactor (a flow rate at 0° C. and 0.1 MPa; cc/sec) (W/$F_0$). The total flow rate of a gas supplied to a reactor refers to the sum of the flow rate of the chlorofluoroethane represented by formula (1) and the flow rate of optionally added inert gas, oxygen, anhydrous hydrogen fluoride, and the like.

The pressure in the dehydrohalogenation step is not particularly limited, and may be atmospheric pressure, an increased pressure of up to 3 MPaG, or a reduced pressure of down to −0.1 MPaG. Of these, atmospheric pressure or a reduced pressure of down to −0.1 MPaG is preferable.

When the dehydrohalogenation step is performed, for example, in a gas phase, the gas after the reaction contains, in addition to the target product (1-chloro-1,2-difluoroethylene) generated through the dehydrohalogenation reaction, a hydrogen halide and a by-product, and may even contain the starting material compound (the compound represented by formula (1)) under certain reaction conditions. The by-product varies depending on the starting material compound (the compound represented by formula (1)) used in the dehydrohalogenation step. For example, when 1-chloro-1,2,2-trifluoroethane is used, chloro-2,2-difluoroethylene (HCFO-1122) represented by the formula CHCl=CF$_2$ and trifluoroethylene (HFO-1123) represented by the formula CHF=CF$_2$ are generated as by-products. When 1-chloro-1,1,2-trifluoroethane is used, trifluoroethylene (HFO-1123) represented by the formula CHF=CF$_2$ is generated as a by-product. When 1,2-dichloro-1,2-difluoroethane is used, 1,2-dichloro-1-fluoroethylene (HCFO-1121) represented by the formula CFCl=CHCl is generated as a by-product. When 1,1-dichloro-1,2-difluoroethane is used, 1,1-dichloro-2-fluoroethylene (HCFO-1121a) represented by CCl$_2$=CHF is generated as a by-product.

After the dehydrohalogenation step, the first method of the present invention may optionally comprise the step of separating the hydrogen halide contained in the gas after the reaction. The method for separating the hydrogen halide is not particularly limited, and may be a known method. When the hydrogen halide is hydrogen fluoride, hydrogen fluoride can be separated from the organic compound containing the target product by, for example, distillation or liquid-liquid separation. When the hydrogen halide is hydrogen chloride, hydrogen chloride can be separated from the organic compound containing the target product by, for example, compressing the gas after the reaction and distilling the compressed gas under increased pressure. Alternatively, hydrogen chloride can be separated from the organic compound containing the target product by performing the dehydrochlorination step under increased pressure and continuously performing distillation under increased pressure. Additionally, the hydrogen halide may be removed, for example, by washing with water; washing with water and distillation may be suitably combined.

After the dehydrohalogenation step, the first method of the present invention may optionally comprise the step of separating the target product (1-chloro-1,2-difluoroethylene) contained in the gas after the reaction from the by-product, and the starting material compound (the compound represented by formula (1)) that may be contained under certain reaction conditions. The method for separating the target product from the by-product and the starting material compound is not particularly limited, and a known method may be used. Examples of such a method include distillation, liquid-liquid separation, and adsorption. When separation by distillation is difficult to perform due to the close boiling points of the target product, the by-product, and the starting material compound that may be contained under certain conditions, an optional component capable of forming azeotrope with the target product or by-product may be added to perform distillation by using azeotropy with the optional component for a separation purpose. The separated starting material compound can be used again in the dehydrohalogenation step (i.e., recyclable).

After the dehydrohalogenation step, the first method of the present invention may optionally comprise the step of separating the generated mixture of the cis form and the trans form of 1-chloro-1,2-difluoroethylene into trans-1-chloro-1,2-difluoroethylene and cis-1-chloro-1,2-difluoroethylene. The method for separating the mixture into the cis form and the trans form is not particularly limited, and may be a known method. For example, the methods for separating the target product from the by-product and the starting material compound described above as examples may be used. Either the separated cis form or the separated trans form may be used, or both of the cis form and the trans form may be individually used for a different application.

When the first method of the present invention comprises two or three steps of the steps described above (i.e., the step of separating the hydrogen halide contained in the gas after the reaction, the step of separating the target product from the by-product and the starting material compound, and the step of separating the mixture into the cis form and the trans form), the order of the steps is not particularly limited, and these steps may be performed in any order.

Second Invention

The present invention also encompasses a method for producing 1-chloro-1,2-difluoroethylene (CFCl=CHF; HCFO-1122a) from chlorotrifluoroethylene (CFCl=CF$_2$; CTFE) and/or 1,1,2-trichloro-1,2,2-trifluoroethane (CFCl$_2$—CF$_2$Cl; CFC-113), which are starting materials. In this specification, the method may be referred to as "the second method of the present invention."

The second method of the present invention comprises the step of reducing a chlorotrifluoroethylene and/or 1,1,2-trichloro-1,2,2-trifluoroethane to generate a chlorotrifluoroethane represented by formula (2) CFClX$^3$—CHFX$^4$ wherein X$^3$ and X$^4$ are different from each other and represent H or F. In this specification, the chlorotrifluoroethane represented by formula (2) may be simply referred to as "chlorotrifluoroethane." In this specification, the step may be referred to as the "first step."

Additionally, the second method of the present invention comprises the step of dehydrofluorinating the chlorotrifluoroethane obtained in the first step. In this specification, this step may be referred to as the "second step."

In the first step, the chlorotrifluoroethane represented by formula (2) is generated by reducing a chlorotrifluoroethylene and/or 1,1,2-trichloro-1,2,2-trifluoroethane.

In the first step, a chlorotrifluoroethylene and/or 1,1,2-trichloro-1,2,2-trifluoroethane are used as a starting material compound. For the starting material compound, either a chlorotrifluoroethylene or 1,1,2-trichloro-1,2,2-trifluoroethane may be used, or these two compounds may be mixed. The mixture ratio in the case of mixing these two compounds is not particularly limited, and can suitably be determined.

The chlorotrifluoroethane represented by formula (2) is specifically 1-chloro-1,2,2-trifluoroethane (HCFC-133) represented by the formula CHFCl—CHF$_2$, or 1-chloro-1,1,2-trifluoroethane (HCFC-133b) represented by the formula CF$_2$Cl—CH$_2$F.

For example, when a chlorotrifluoroethylene and hydrogen are used respectively as a starting material compound and a reducing agent in the first step, the reduction reaction shown in the following reaction scheme (1) proceeds.

$$CF_2=CFCl+H_2(\text{hydrogenation catalyst}) \rightarrow CHF_2—CHFCl \qquad (1)$$

When 1,1,2-trichloro-1,2,2-trifluoroethane is used, and hydrogen is used as a reducing agent in the first step, the reduction reaction shown in the following reaction scheme (2) proceeds.

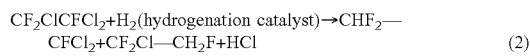

$$CF_2ClCFCl_2 + H_2 \text{(hydrogenation catalyst)} \rightarrow CHF_2-CFCl_2 + CF_2Cl-CH_2F + HCl \quad (2)$$

The first step may be performed in a liquid phase or a gas phase, and is preferably performed in a gas phase.

The first step is preferably performed using a reducing agent. The reducing agent for use may be a known agent. Examples of the reducing agent include hydrogen, sodium borohydride, and hydrazine. The first step is also preferably performed using a reduction catalyst. The reduction catalyst is not particularly limited, and may be a known catalyst. For example, the reduction catalyst for use may be a precious metal catalyst, such as platinum, palladium, rhodium, and ruthenium, or a metal catalyst, such as nickel and zirconium, with a precious metal catalyst being particularly preferable. It is also preferable to subject the reduction catalyst to a reduction treatment with hydrogen beforehand from the standpoint of, for example, stable catalytic activity.

The reduction catalyst for use may be supported on a carrier. Such a carrier is not particularly limited, and may be a known carrier. Examples of the carrier include alumina, activated carbon, and zeolite. The method for having a reduction catalyst supported on a carrier is not particularly limited, and may be known method. For example, a conventional method for preparing a precious metal catalyst may be used. Preferable examples of the reduction catalyst supported on a carrier include a palladium catalyst supported on activated carbon.

The ratio of the starting material compound and the reducing agent in the first step can suitably be determined according to the type of the starting material for use, the type of the generated target product, etc. For example, when 1,1,2-trichloro-1,2,2-trifluoroethane and hydrogen are used respectively as a starting material compound and a reducing agent, 2-fold mols of hydrogen ($H_2$) (stoichiometric amount) is typically used to remove two chlorine atoms of 1,1,2-trichloro-1,2,2-trifluoroethane through reduction to thereby obtain 1-chloro-1,2,2-trifluoroethane and/or 1-chloro-1,1,2-trifluoroethane. To fully complete the reaction, hydrogen in an excessive amount, which is larger than the stoichiometric amount based on the total number of mols of the starting material compound (e.g., more than 5-fold mols), is required. However, the use of hydrogen in an amount excessively larger than the stoichiometric amount is not preferable because the use of hydrogen in such an amount increases a by-product formed by losing undue chlorine atoms or fluorine atoms through reduction. Thus, it is preferable to determine the amount of hydrogen within the range of 2-fold mols or more to 5-fold mols or less.

Hydrogen in an amount smaller than the stoichiometric amount based on the total number of mols of the starting material compound (e.g., less than 2-fold mols of hydrogen) may be used. The amount is, for example, 1-fold mol or more to less than 2-fold mols. When the amount of hydrogen is so, the starting material compound, an intermediate formed by losing only one chlorine atom through reduction (e.g., 2,2-dichloro-1,1,1-trifluoroethane ($CHCl_2-CF_3$; HCFC-123)), etc. remain. These compounds can be recovered in accordance with a standard method and supplied to the first step.

When chlorotrifluoroethylene and hydrogen are used respectively as a starting material compound and a reducing agent, 1 mol of hydrogen (stoichiometric amount) is typically used to obtain 1-chloro-1,2,2-trifluoroethane. To fully complete the reaction, a slightly excessive amount of hydrogen (e.g., more than 1-fold mol to 2-fold mols) is preferably used. To control the generation of reaction heat, hydrogen in an amount equal to or smaller than the stoichiometric amount may be used. When this is the case, the remaining starting material compound can be recovered and supplied to the first step.

When the first step is performed in a gas phase, the reaction temperature is not particularly limited and can suitably be determined, as long as the reaction for generating the chlorotrifluoroethane represented by formula (2) from the starting material compound can occur. For example, when the first step is performed in a gas phase, the reaction temperature is typically about 70 to 350° C., and preferably about 80 to 200° C. When a chlorotrifluoroethylene is used as a starting material compound, the reaction temperature is preferably lower than the reaction temperature when 1,1,2-trichloro-1,2,2-trifluoroethane is used as a starting material compound.

The reaction time in the first step is not particularly limited. For example, when the first step is performed in a gas phase, the contact time may be about 0.1 to 30 g·sec/cc, and preferably about 1 to 20 g·sec/cc: the contact time is represented by the ratio of the amount of a packed catalyst W (g) to the total amount of a starting material gas $F_0$ supplied to the reaction system (a flow rate at 0° C. and 1 atm; cc/sec) ($W/F_0$). The contact time within these numerical ranges is preferable because an overly short contact time may result in a failure to fully convert the starting material, while an overly long contact time may lead to the generation of a by-product resulting from an accelerated reaction of the starting material compound, decomposition to $C_1$ compounds, etc.

When the first step is performed in a liquid phase, a solvent may be used. The solvent includes water; alcohols, such as ethanol, and isopropyl alcohol; acetic acid, ethyl acetate; glyme, such as diglyme; and pyridine. The first step may also be performed in the absence of a solvent. When the reaction in the first step is performed in a liquid phase, the reaction temperature is preferably about 0 to 150° C., with the reaction pressure preferably being ordinary pressure to about 5 MPa.

When the first step is performed, for example, in a gas phase, the gas after the reaction contains, in addition to the target product (chlorotrifluoroethane represented by formula (2)) generated through a reduction reaction, hydrogen chloride, and a by-product, and may even contain hydrogen and the starting material compound (chlorotrifluoroethylene and/or 1,1,2-trichloro-1,2,2-trifluoroethane) under certain reaction conditions. The by-product varies depending on the starting material compound used in the first step. For example, when 1,1,2-trichloro-1,2,2-trifluoroethane is used, 2,2-dichloro-1,1,1-trifluoroethane (HCFC-123) represented by the formula $CHCl_2-CF_3$ etc. are generated as by-products. When a chlorotrifluoroethylene is used, 1,1,2-trifluoroethane (HFC-143) represented by the formula $CHF_2-CH_2F$ etc. are generated as by-products.

After the first step, the second method of the present invention may optionally comprise the step of separating the hydrogen chloride contained in the gas after the reaction. The method for separating hydrogen chloride is not particularly limited, and may be a known method. Hydrogen chloride can be separated from the organic compound containing the target product by, for example, compressing the gas after the reaction and distilling the compressed gas under increased pressure. Alternatively, hydrogen chloride can be separated from the organic compound containing the target product by performing the first step under increased pressure and continuously performing distillation under increased pressure. Additionally, hydrogen chloride may be removed, for example, by washing with water; washing with water and distillation may also suitably be combined.

In the second step, 1-chloro-1,2-difluoroethylene is obtained by dehydrofluorinating the chlorotrifluoroethane represented by formula (2) obtained in the first step. The second step is preferably performed in a gas phase.

In the second step, only one compound of the two compounds listed as the chlorotrifluoroethane represented by formula (2), or the combination of the two compounds, may be used. The mixture ratio of the two compounds in the combination is not particularly limited, and can suitably be determined.

This second step corresponds to the dehydrohalogenation step in the first invention of the present invention described above. To be more specific, the chlorofluoroethane represented by formula (1) (the starting material in the first invention of the present invention) that is the compound wherein $X^1$ is H, and $X^2$ is F, or that is the compound wherein $X^1$ is F, and $X^2$ is H corresponds to the chlorotrifluoroethane represented by formula (2).

The second step may be performed in the presence of a catalyst or in the absence of a catalyst. Performing the second step in the presence of a catalyst is preferable because doing so can increase the selectivity for and the yield of 1-chloro-1,2-difluoroethylene.

When the second step is performed in the presence of a catalyst, the catalyst for use is not particularly limited, and may be a known catalyst that exhibits catalytic activity in the dehydrofluorination reaction. Such a catalyst includes dehydrofluorination catalysts.

Examples of dehydrofluorination catalysts include halides, oxides, and fluorinated oxides of metals, such as transition metals, aluminum, elemental metals that belong to group 14, and elemental metals that belong to group 15. These dehydrofluorination catalysts are considered to have an effect of accelerating dehydrofluorination reaction due to the high affinity of the metal elements for the detached fluorine atom.

Examples of transition metals include titanium, vanadium, chromium, manganese, iron, cobalt, nickel, niobium, molybdenum, tantalum, and zirconia. Examples of elemental metals that belong to group 14 include tin and lead. Examples of elemental metals that belong to group 15 include arsenic, antimony, and bismuth. Examples of halides include fluorides and chlorides.

Specific examples of halides of the metals described above include titanium(IV) chloride, chromium(III) fluoride, chromium(III) chloride, iron(III) chloride, niobium(V) chloride, molybdenum(V) chloride, tantalum(V) chloride, aluminum fluoride, tin(IV) chloride, antimony(V) fluoride, antimony(V) chloride, and antimony(III) chloride. Specific examples of oxides of the metals described above include chromium(III) oxide and aluminum oxide. Specific examples of fluorinated oxides of the metals described above include fluorinated chromium(III) oxide and fluorinated aluminum oxide.

Of the dehydrofluorination catalysts listed above, in particular, chromium(III) oxide, aluminum oxide, fluorinated chromium(III) oxide, and fluorinated aluminum oxide are preferable. Chromium(III) oxide and fluorinated chromium(III) oxide for use may be in the form of crystalline chromium oxide, amorphous chromium oxide, and the like.

The dehydrofluorination catalysts may be used singly or in any combination of two or more.

The dehydrofluorination catalysts for use may be supported on a carrier. Such a carrier is not particularly limited, and may be a known carrier for use in dehydrofluorination catalysts. Examples of carriers include porous aluminosilicate, such as zeolite, aluminum oxide, silicon oxide, activated carbon, titanium oxide, zirconia oxide, zinc oxide, and aluminum fluoride. The carriers may be used singly or in the form of composite composed of two or more carriers. Examples of the combination of a dehydrofluorination catalyst and a carrier (a dehydrofluorination catalyst on a carrier) include chromium(III) oxide on aluminum oxide, chromium (III) oxide on aluminum fluoride, and chromium(III) oxide on activated carbon. Examples of the combination of two dehydrofluorination catalysts and a carrier (a dehydrofluorination catalyst and a dehydrofluorination catalyst on a carrier) include cobalt(II) chloride and chromium(III) oxide on aluminum oxide, and nickel(II) chloride and chromium (III) oxide on aluminum oxide.

The second step is preferably performed in a reactor. The reactor is not particularly limited. For example, a continuous reactor, such as an adiabatic reactor, and a multitubular reactor heated with a heating medium, may be used. The reactor is also preferably made of a material resistant to the corrosive action of hydrogen fluoride generated in the dehydrofluorination reaction.

When a catalyst is used in the second step, the method for allowing the catalyst to be present in the reactor is not particularly limited, as long as the starting material sufficiently comes into contact with the catalyst. Examples of the method include a method by which a reactor is packed with a catalyst.

When a catalyst is used in the second step, the chlorotrifluoroethane represented by formula (2) and a catalyst are brought into contact with each other. The method for bringing the chlorotrifluoroethane represented by formula (2) and a catalyst into contact with each other is not particularly limited. For example, the chlorotrifluoroethane represented by formula (2) and a catalyst can be brought into contact by supplying the chlorotrifluoroethane represented by formula (2) to the reactor in a gas phase.

The chlorotrifluoroethane represented by formula (2) may be supplied as is to a reactor, or may be supplied to a reactor together with a gas inert to the starting material, the catalyst, etc. when the chlorotrifluoroethane must be diluted for some reason, for example, to control the reactivity. Examples of the inert gas include nitrogen, helium, and argon.

When the chlorotrifluoroethane represented by formula (2) is supplied to a reactor together with an inert gas, the concentration of the inert gas is not particularly limited. For example, the concentration of the inert gas may be 10 to 99 mol % of the total amount of the gas component supplied to the reactor.

When a catalyst is used in the second step, oxygen may be supplied to a reactor to maintain the catalytic activity for an extended period of time. The oxygen supplied to the reactor may be an oxygen gas alone or air containing oxygen. The amount of oxygen supplied may be, for example, about 0.1 to 50 mol %, and preferably 1 to 20 mol % of the total amount of the gas component supplied to the reactor.

Additionally, when a catalyst is used in the second step, anhydrous hydrogen fluoride may be supplied to the reactor, for example, for the purpose of increasing the catalytic activity of the dehydrofluorination catalyst. The amount of anhydrous hydrogen fluoride supplied may be about 1 to 100 mols per mol of the chlorotrifluoroethane represented by formula (2) supplied to a reactor.

The reaction temperature in the second step is not particularly limited, as long as the reaction to generate 1-chloro-1,2-difluoroethylene from the chlorotrifluoroethane represented by formula (2) occurs. The specific reaction temperature is, for example, about 200 to 550° C., preferably about 250 to 450° C., and more preferably about 300 to 450° C. The reaction temperature within these ranges can maintain excellent conversion of the starting material, and easily reduces the generation of impurities and deterioration of catalytic activity caused by the altered catalyst. A higher reaction temperature is likely to generate trans-1-chloro-1,2-difluoroethylene. Thus, if a higher selectivity for the trans form of 1-chloro-1,2-difluoroethylene is desired, the reaction temperature is preferably 300° C. or more.

The reaction time in the second step is not particularly limited. When the second step is performed in the absence of a catalyst, the retention time is preferably about 1 to 500 sec, and more preferably 30 to 300 sec: the retention time is represented by the ratio of volume V (cc) of a heated reactor to the total flow rate $F_0$ of a gas supplied to the reactor (a flow rate at 0° C. and 0.1 MPa; cc/sec) ($V/F_0$). When the second step is performed in the presence of a catalyst, the contact time is preferably about 1 to 500 g·sec/cc, and more preferably about 30 to 300 g·sec/cc: the contact time is represented by the ratio of the amount of a packed catalyst W (g) to the total flow rate $F_0$ of a gas supplied to a reactor (a flow rate at 0° C. and 0.1 MPa; cc/sec) ($W/F_0$). The total flow rate of a gas supplied to a reactor refers to the sum of the flow rate of the chlorotrifluoroethane represented by formula (2) and, if added, the flow rate of inert gas, oxygen, anhydrous hydrogen fluoride, and the like.

The pressure in the second step is not particularly limited, and may be atmospheric pressure, increased pressure of up to 3 MPaG, or reduced pressure of down to −0.1 MPaG. Of these, atmospheric pressure or reduced pressure of down to −0.1 MPaG is preferable.

When the second step is performed, for example, in a gas phase, the gas after the reaction contains, in addition to the target product (1-chloro-1,2-difluoroethylene) generated through the dehydrofluorination reaction, hydrogen fluoride and a by-product, and may even contain the starting material compound (the compound represented by formula (2)) under certain reaction conditions. The by-product varies depending on the starting material compound (the compound represented by formula (2)) used in the second step. For example, when 1-chloro-1,2,2-trifluoroethane is used, chloro-2,2-difluoroethylene (HCFO-1122) represented by the formula $CHCl=CF_2$ and trifluoroethylene (HFO-1123) represented by the formula $CHF=CF_2$ are generated as by-products. When 1-chloro-1,1,2-trifluoroethane is used, trifluoroethylene (HFO-1123) represented by the formula $CHF=CF_2$ is generated as a by-product.

After the second step, the second method of the present invention may optionally comprise the step of separating the hydrogen fluoride contained in the gas after the reaction. The method for separating hydrogen fluoride is not particularly limited, and may be a known method. Hydrogen fluoride can be separated from the organic compound containing the target product by, for example, distillation or liquid-liquid separation. Additionally, hydrogen fluoride may be removed, for example, by washing with water; and washing with water and distillation may suitably be combined.

After the second step, the second method of the present invention may optionally comprise the step of separating the target product (1-chloro-1,2-difluoroethylene) contained in the gas after the reaction from the by-product, and the starting material compound (the compound represented by formula (2)) that may be contained under certain reaction conditions. The method for separating the target product from the by-product and the starting material compound is not particularly limited, and may be a known method. Examples of such a method include distillation, liquid-liquid separation, and adsorption. When separation by distillation is difficult to perform due to the close boiling points of the target product, the by-product, and the starting material compound that may be contained under certain conditions, an optional component capable of forming azeotrope with the target product or by-product may be added to perform distillation by using azeotropy with the optional component for the purpose of separation. The separated starting material compound can be used again in the dehydrofluorination step (i.e., recyclable).

After the dehydrofluorination step, the second method of the present invention may optionally comprise the step of separating the generated mixture of the cis form and the trans form of 1-chloro-1,2-difluoroethylene into trans-1-chloro-1,2-difluoroethylene and cis-1-chloro-1,2-difluoroethylene. The method for separating the mixture into the cis form and the trans form is not particularly limited, and may be a known method. For example, the methods for separating the target product from the by-product and the starting material compound described above as examples may be used. Either the separated cis form or the separated trans form may be used, or both of the cis form and the trans form may be individually used for a different application.

When the second method of the present invention comprises two or three steps of the steps described above (i.e., the step of separating the hydrogen fluoride contained in the gas after the reaction, the step of separating the target product from the by-product and the starting material compound, and the step of separating the mixture into the cis form and the trans form), the order of the steps is not particularly limited, and these steps may be performed in any order.

The reactions in the first step and the second step can be continuously performed in a gas phase. Performing the first and second steps in this manner has some advantages, such as the elimination of the need for equipment for storing the product of the first step, and saving heat energy by recycling the heat energy used in the first step in the second step.

EXAMPLES

The following describes the present invention in detail with reference to Examples. However, the present invention is not limited to the embodiments of the Examples.

Example 1

A tubular Hastelloy reactor (inner diameter: 15 mm, length: 1 m) was packed with 20.0 g of a palladium catalyst supported on activated carbon (amount of the support: 0.5 mass %). The reactor was maintained at atmospheric pressure (0.1 MPa) and at 150° C., and hydrogen gas at a flow rate of 60 cc/min (flow rate at 0° C. and 0.1 MPa; the same applies hereinafter), chlorotrifluoroethylene (CTFE) gas at a flow rate of 60 cc/min, and nitrogen gas at a flow rate of 480 cc/min were supplied to the reactor. The reactor was then maintained for 2 hours. The gas at the outlet of the reactor was analyzed by gas chromatography (GC). $CHF_2CHFCl$ was obtained as follows: CTFE conversion: 64%; selectivity for $CHF_2CHFCl$: 62%; $CHF_2CH_2F$: 25%; $CH_2FCH_2F$: 5%; others: 8%.

Example 2

A tubular Hastelloy reactor (inner diameter: 15 mm, length: 1 m) was packed with 20.0 g of a γ-alumina catalyst (specific surface area: 400 m²/g), which is aluminum oxide. The reactor was maintained at atmospheric pressure (0.1 MPa) and at 350° C., and CHF$_2$CHFCl gas at a flow rate of 4 cc/min and nitrogen gas at a flow rate of 20 cc/min were supplied to the reactor. The reactor was then maintained for 2 hours. The gas at the outlet of the reactor was analyzed by GC. CHF=CFCl was obtained as follows: CHF$_2$CHFCl conversion: 82%; selectivity for CHF=CFCl: 80%; CHF=CHF: 11%; others: 9%.

Example 3

A tubular Hastelloy reactor (inner diameter: 15 mm, length 1 m) was packed with 20.0 g of a magnesium fluoride catalyst (specific surface area: 15 m²/g). The reactor was maintained at atmospheric pressure (0.1 MPa) and at 450° C., and CHFClCHFCl gas at a flow rate of 4 cc/min, and nitrogen gas at a flow rate of 20 cc/min were supplied to the reactor. The reactor was then maintained for 2 hours. The gas at the outlet of the reactor was analyzed by GC. CHF=CFCl was obtained as follows: CHFClCHFCl conversion: 56%; selectivity for CHF=CFCl: 82%; CHF=CHF: 12%; others: 6%.

The invention claimed is:

1. A method for producing 1-chloro-1,2-difluoroethylene, the method comprising the step of
    dehydrohalogenating, in the presence of a catalyst, a chlorofluoroethane represented by formula (1):

CFClX$^1$—CHFX$^2$ wherein X$^1$ and X$^2$ are different from each other and represent H, F, or Cl; and either X$^1$ or X$^2$ is H, and
        wherein the catalyst is:
            at least one member selected from the group consisting of halides, oxides, and fluorinated oxides of at least one selected from the group consisting of transition metals, aluminum, elemental metals that belong to group 14, and elemental metals that belong to group 15, and/or
            at least one member selected from the group consisting of halides, oxides, and fluorinated oxides of at least one selected from the group consisting of alkaline earth metals, and divalent or monovalent transition metals, and/or
            activated carbon.

2. The method according to claim 1, wherein the dehydrohalogenation step is performed in a gas phase.

3. The method according to claim 1, wherein the chlorofluoroethane is at least one member selected from the group consisting of 1-chloro-1,2,2-trifluoroethane, 1-chloro-1,1,2-trifluoroethane, 1,2-dichloro-1,2-difluoroethane, and 1,1-dichloro-1,2-difluoroethane.

4. A method for producing 1-chloro-1,2-difluoroethylene, the method comprising the step of
    dehydrohalogenating in a gas phase, and in the absence of a catalyst, a chlorofluoroethane represented by formula (1):

CFClX$^1$—CHFX$^2$ wherein X$^1$ and X$^2$ are different from each other and represent H, F, or and either X$^1$ or X$^2$ is H.

5. The method according to claim 1, wherein the dehydrohalogenation step is performed at a temperature of 200 to 550° C.

6. The method according to claim 1, wherein the chlorofluoroethane is 1-chloro-1,2,2-trifluoroethane and/or 1-chloro-1,1,2-trifluoroethane, and the dehydrohalogenation step is a dehydrofluorination step.

7. A method for producing 1-chloro-1,2-difluoroethylene, the method comprising the steps of
    reducing a chlorotrifluoroethylene and/or 1,1,2-trichloro-1,2,2-trifluoroethane to generate a chlorotrifluoroethane represented by formula (2):

CFClX$^3$—CHFX$^4$ wherein X$^3$ and X$^4$ are different from each other and represent H or F, and
    dehydrofluorinating, in the presence of a catalyst, the chlorotrifluoroethane obtained in the previous step,
        wherein the catalyst is at least one member selected from the group consisting of halides, oxides, and fluorinated oxides of at least one selected from the group consisting of transition metals, aluminum, elemental metals that belong to group 14, and elemental metals that belong to group 15.

* * * * *